United States Patent
King

(10) Patent No.: US 6,837,987 B1
(45) Date of Patent: Jan. 4, 2005

(54) CARBON MONOXIDE SENSOR

(75) Inventor: Walter John King, Totnes (GB)

(73) Assignee: Dart Sensors Limited, Devon (GB)

( * ) Notice: Subject to any disclaimer, the term of this patent is extended or adjusted under 35 U.S.C. 154(b) by 310 days.

(21) Appl. No.: 10/009,516

(22) PCT Filed: Jun. 15, 2000

(86) PCT No.: PCT/GB00/02348
§ 371 (c)(1),
(2), (4) Date: Mar. 4, 2002

(87) PCT Pub. No.: WO00/77505
PCT Pub. Date: Dec. 21, 2000

(30) Foreign Application Priority Data

Jun. 15, 1999 (GB) .............................................. 9913946

(51) Int. Cl.$^7$ ........................................... G01N 27/413
(52) U.S. Cl. .................... 205/783; 205/782; 205/782.5; 204/431
(58) Field of Search ............................. 205/782, 782.5, 205/783; 204/409, 415, 431, 432

(56) References Cited

U.S. PATENT DOCUMENTS 5,080,867 A * 1/1992 Cooke ......................... 422/86
5,667,653 A * 9/1997 Schneider et al. .......... 204/431
5,985,673 A * 11/1999 Bao et al. .................... 436/151

OTHER PUBLICATIONS

CAPLUS abstract for Yarym–Agaeva et al (Gigiena Truda i Professional'nye Zabolevaniya (1986), (9), pp. 55–56).*

* cited by examiner

Primary Examiner—Kaj K. Olsen
(74) Attorney, Agent, or Firm—Nath & Associates; Harold L. Novick

(57) ABSTRACT

A method and apparatus for detecting the presence of carbon monoxide in a gas which may also contain contaminating substances uses a pre-treatment means to absorb contaminating substances and to convert them to non-contaminating substances.

12 Claims, 1 Drawing Sheet

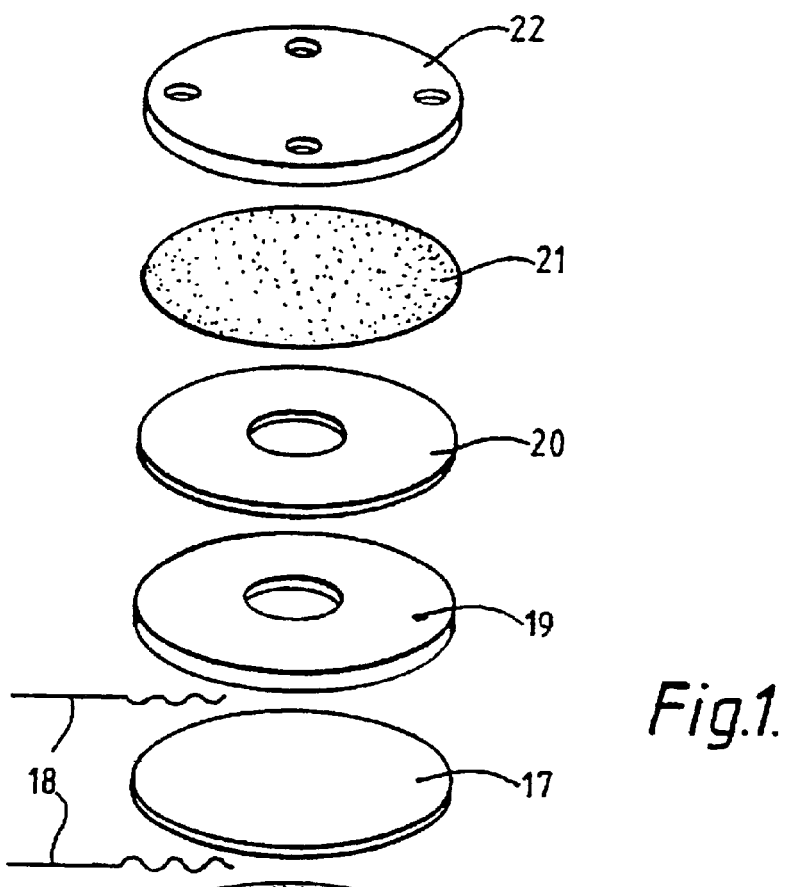
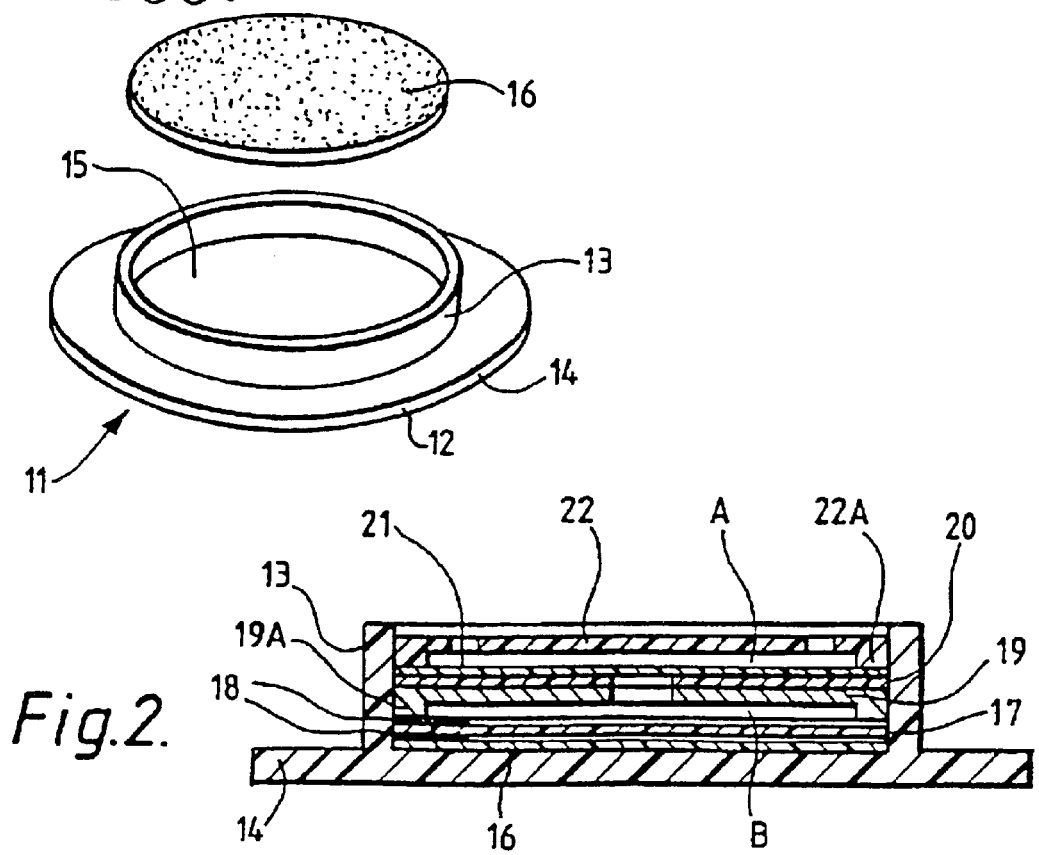
Fig.1.
Fig.2.

CARBON MONOXIDE SENSOR

This invention relates to apparatus for detection of carbon monoxide.

Among the available methods of detecting carbon monoxide, electrochemical sensors have shown great promise as they are relatively cheap, sensitive and reliable. However, they suffer the disadvantage that they are inherently sensitive to a wide range of substances and as a result are liable to give erroneous responses in service.

It is an object of the present invention to provide a carbon monoxide sensor which is of enhanced specificity compared with electrochemical sensors and which preferably does not require a source of power.

According to one aspect of the present invention, a carbon monoxide sensor comprises pre-treatment means and sensor means, the pre-treatment means comprising means to absorb contaminating substances and means to convert contaminating substances to non-contaminating substances.

By "contaminating substances" is meant elements or compounds in gaseous or vapour form which if incident on the sensor means would themselves be detected and which could thus give rise to an erroneous or misleading result of carbon monoxide presence or concentration.

Preferably, the pre-treatment and sensor means are contained in separate chambers which are in mutual communication, the pretreatment chamber including access means for the gaseous test substrate.

The sensor means may comprise an electrochemical sensor preferably of the fuel cell type and comprising two electrochemically-active electrodes separated by an electrolyte absorbed on a porous substrate. The electrodes are electrically connected to a display device by current-carrying leads which preferably comprise platinum wire. The sensor electrodes may comprise a precious metal as catalyst, optionally disposed on a suitable support or, alternatively, applied direct to the electrode surface in finely-divided form such as platinum black. The porous substrate may comprise a plastics polymeric material such as polyvinyl chloride or polyethylene and the electrolyte is preferably acidic, such as sulphuric acid at a concentration between 0.1 and 10M.

The absorption pre-treatment means is preferably an aqueous medium, since most of the common contaminating substances including ammonia, sulphur dioxide, hydrogen sulphide, ethanol and other organic contaminants such as other alcohols and aldehydes, as well as acidic and alkaline gaseous substances, are soluble or highly soluble in water.

The partition coefficients between air and water for the above compounds are as follows: ammonia 0.0014 (20° C.); sulphur dioxide 0.0125 (20° C.); hydrogen sulphide 0.37 (20°) and ethanol 0.0004 (34° C.). By contrast, carbon monoxide has a partition coefficient of 45 (20° C.) and thus is predominantly non-absorbed by an aqueous pre-treatment means.

To inhibit evaporation and to prevent eventual drying, the aqueous medium preferably contains sulphuric acid or other water-retention substance.

The aqueous medium is preferably itself absorbed on a solid absorbent matrix such as porous polyethylene, polyvinyl chloride or other inert plastics material.

The function of the conversion pre-treatment means is to oxidise the absorbed contaminating substances which would otherwise accumulate in and eventually saturate the absorption medium. The conversion means is preferably chemically catalytically active to avoid the need for a source of power, the catalyst is preferably a heterogeneous catalyst comprising platinum or other precious metal which may be dispersed on a support material such as activated carbon or a zeolite provided that the catalyst is not thereby made active for carbon monoxide oxidation. However, the preferred catalyst is finely divided platinum metal such as platinum black.

Preferably, the sensor includes a porous barrier to exclude airborne particulates from the pre-treatment means.

In another embodiment, the invention provides a method for sensing the presence of carbon monoxide in a gaseous test substrate which may also contain contaminating substances, the method comprising pre-treating the substrate to absorb any contaminating substances and to convert said contaminating substances to non-contaminating substances and testing the residue of the test substrate for the presence of carbon monoxide.

Embodiments of the invention will now be described by way of example with reference to the accompanying drawings, of which FIG. 1 is an exploded view of the component parts of a carbon monoxide sensor and FIG. 2 is a cross sectional view of the sensor made from the parts shown in FIG. 1.

Referring firstly to FIG. 1, the sensor device has a base housing 11 in the form of a circular plate 12 having an upstanding annular wall 13 defining an outer annular flange 14 and a central circular cavity 15. At the bottom of the cavity is placed a circular disc 16 of porous polyvinyl chloride containing 5M sulphuric acid solution absorbed therein and the electrodes are placed thereon. The electrodes are constituted by a porous polyvinyl chloride disc 17 with 5M sulphuric acid absorbed therein and coated on its surfaces with respective catalytic layers of platinum black, the upper surface being the working electrode for electrochemical oxidation of carbon monoxide and the lower surface being the counter-electrode to complete the electrochemical circuit by reduction of oxygen. Connecting wires 18 pass the electricity generated to a warning or displace device (not shown).

Over the working electrode is placed an impervious annular disc 19 having a depending outer flange 19A which spaces the disc 19 from the working electrode to form a sensor chamber B (FIG. 2). The disc carries an annular sheet of porous polyvinyl chloride 20 having dilute sulphuric acid absorbed therein and carrying a catalytic surface coating of platinum black. A circular disc or membrane 21 of porous PTFE overlies the sheet 20 and acts as a barrier layer to exclude particulates, and a top plate 22 having holes formed therein is inserted at the top of the cavity 15. The plate 22 has a depending outer flange 22A which spaces the plate from the barrier layer to form in conjunction with the barrier layer and annular sheet 20 a pretreatment chamber A.

In use, ambient air passes by diffusion through the holes in plate 22 into pretreatment chamber A where it initially passes through the interstices of disc 21 to reach the pre-treatment element 20. Most contaminating substances are trapped in element 20 by absorption and catalytic oxidation and carbon monoxide molecules pass through the central hole in the pretreatment element 20, in registration with the central hole in disc 19, into the sensor chamber B. The carbon monoxide is oxidised to carbon dioxide on the upper catalytic surface, the resulting electrical output being proportional to the carbon monoxide concentration. The circular disc 16 containing absorbed sulphuric acid acts as a reservoir which feeds or drains the sensor electrode as the volume of electrolyte expands and contracts with temperature and humidity changes.

What is claimed is:

1. Carbon monoxide sensor apparatus comprising
   a pre-treatment means which comprises
      an aqueous medium to absorb contaminating substances from a gaseous test substrate and
      catalytic means to convert contaminating substances to non-contaminating substance at ambient temperatures; and
   a sensor that senses the presence of carbon monoxide.

2. apparatus according to claim 1, in which the pretreatment and sensor means are contained in separate chambers in mutual communication, the pretreatment chamber including access means for the gaseous test substrate.

3. Apparatus according to claim 1, in which the sensor means comprise an electrochemical sensor comprising two electrochemically-active electrodes separated by an electrolyte absorbed on a porous substrate.

4. Apparatus according to claim 3, in which the sensor electrodes comprise a precious metal as catalyst.

5. Apparatus according to claim 4, in which the catalyst is disposed on a porous support.

6. Apparatus according to claim 4, in which the catalyst is applied direct to the electrode surface in finely-divided form.

7. Apparatus according to claim 3, in which the porous substrate comprises a plastics polymeric material.

8. Apparatus according to claim 3, in which the electrolyte is acidic.

9. Apparatus according to claim 1, in which the aqueous medium contains sulphuric acid or other water-retention substance.

10. Apparatus according to claim 1, in which the aqueous medium is absorbed on a solid absorbent matrix.

11. Apparatus according to claim 1 and including a porous barrier to exclude airborne particulates from the pretreatment means.

12. A method for sensing the presence of carbon monoxide in a gaseous test sample which may also contain contaminating substances, the method comprising
   pre-treating the sample by passage thereof through an aqueous medium to absorb any contaminating substances and over a catalyst at ambient temperatures to convert said contaminating substances to non-contaminating substances and
   testing said pre-treated sample for the presence of carbon monoxide.

* * * * *